United States Patent [19]

Strike

[11] 4,038,308

[45] July 26, 1977

[54] PROSTAGLANDIN DERIVATIVES

[75] Inventor: Donald P. Strike, St. Davids, Pa.

[73] Assignee: American Home Products Corporation, New York, N.Y.

[21] Appl. No.: 722,458

[22] Filed: Sept. 13, 1976

[51] Int. Cl.$^2$ .......................................... C07C 177/00
[52] U.S. Cl. .............................. 260/514 D; 260/340.4; 260/468 D; 260/429.7; 260/488 R; 424/305; 424/317
[58] Field of Search ....................... 260/468 D, 514 D

[56] References Cited

U.S. PATENT DOCUMENTS 4,001,315  1/1977  Strike .................................... 260/514

Primary Examiner—Robert Gerstl
Attorney, Agent, or Firm—Robert Wiser

[57] ABSTRACT

Derivatives of 11-deoxy-PGE$_1$ and 11-deoxy-PGE$_2$ are prepared. These new compounds not heretofore found in nature possess various pharmacological activities, one of which is bronchodilation.

2 Claims, 2 Drawing Figures

FIGURE I
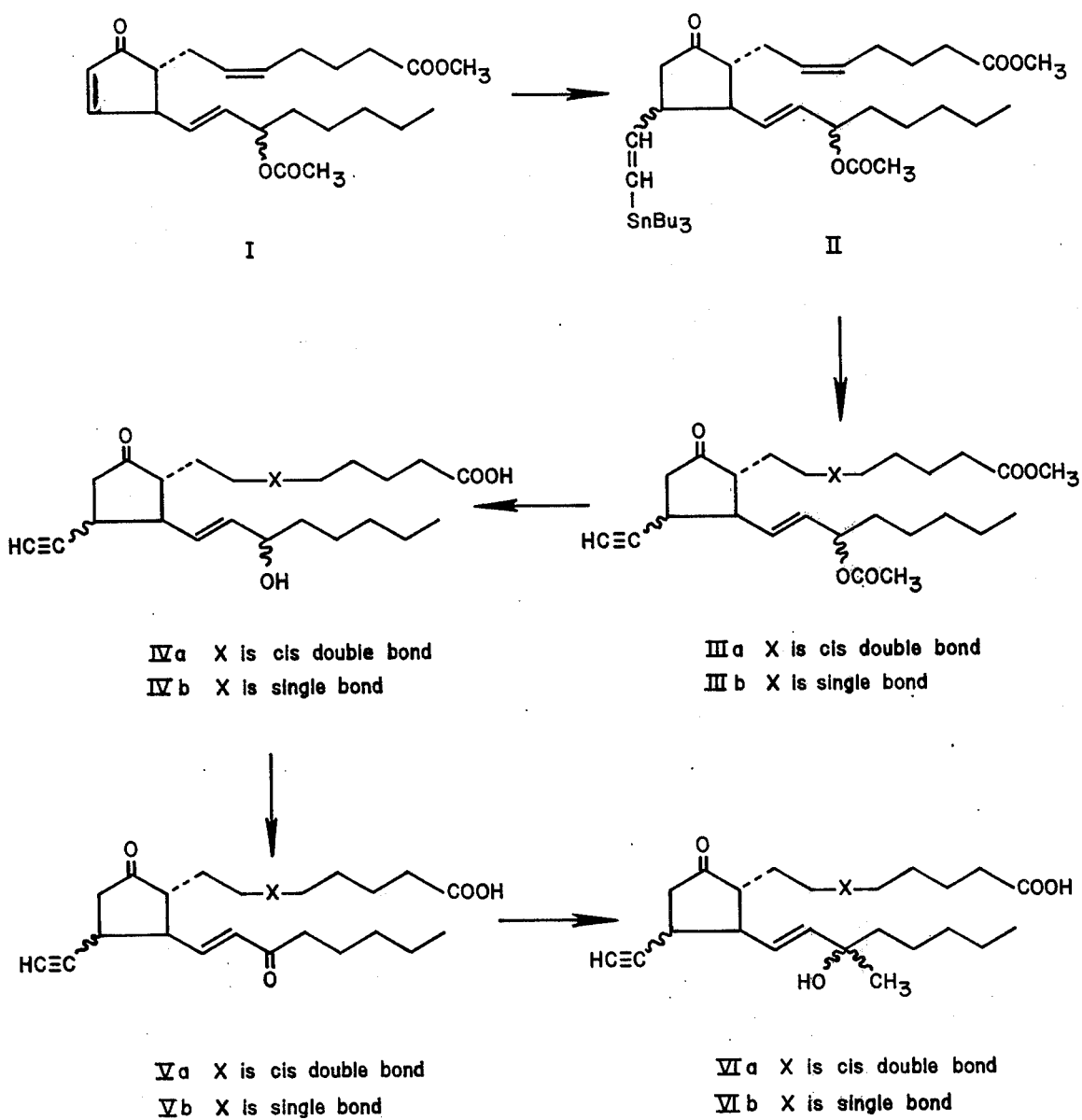

FIGURE II
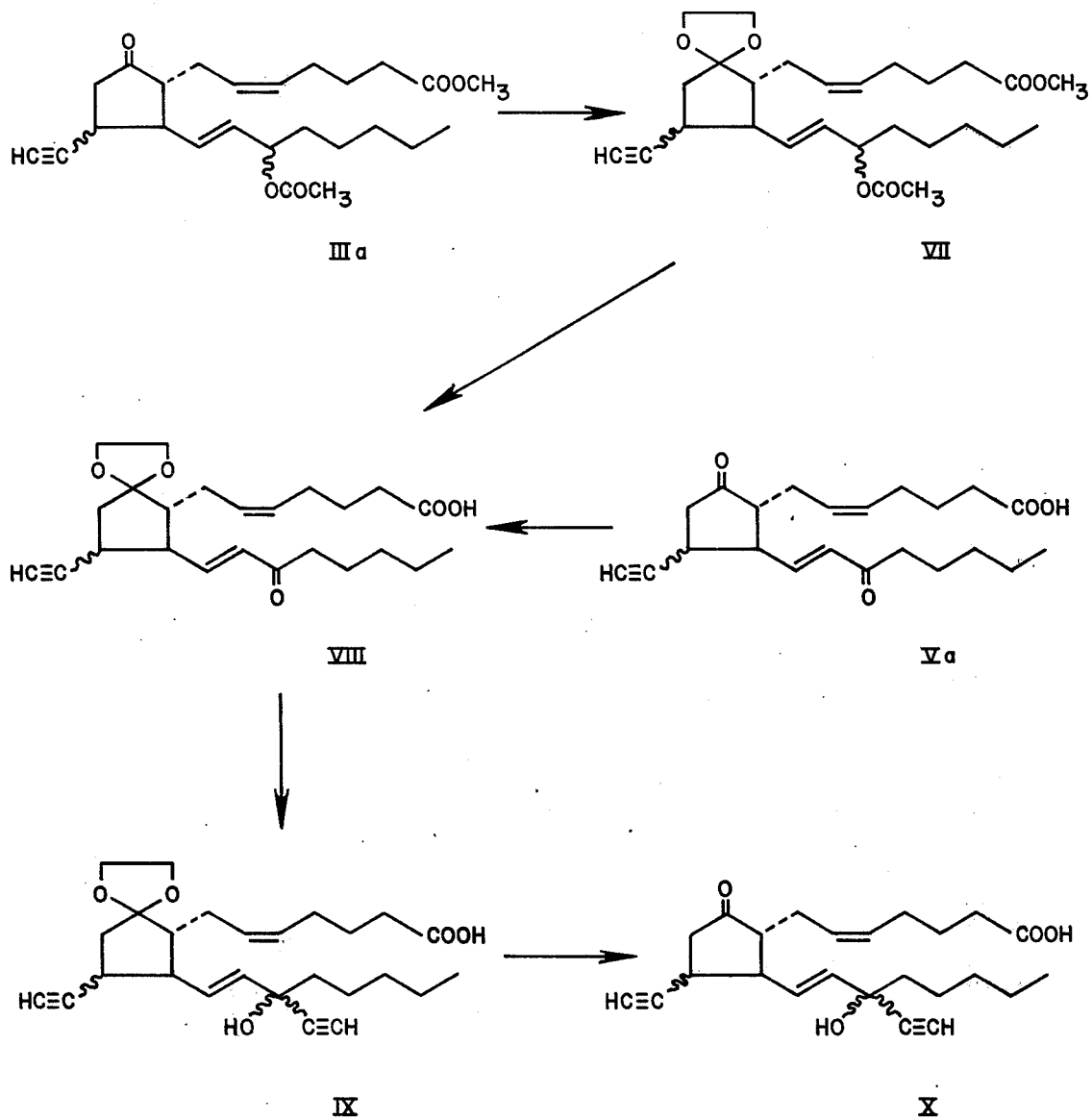

PROSTAGLANDIN DERIVATIVES

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation and the ability to reduce gastric secretion.

The present invention concerns prostaglandin $E_1$ and prostaglandin $E_2$ ($PGE_1$ and $PGE_2$) derivatives in which the 9-position (using the prostanoic acid numbering system) remains intact as a carbonyl group; the 11-position bears an ethynyl group, i.e. the 11-hydroxyl group normally present in $PGE_1$ and $PGE_2$ has been removed and is replaced with an ethynyl group; and there is either a methyl or an ethynyl group at the 15-position in addition to the normally present hydroxyl group.

SUMMARY OF THE INVENTION

The invention sought to be patented in a first composition aspect resides in the concept of a chemical compound of the structure:

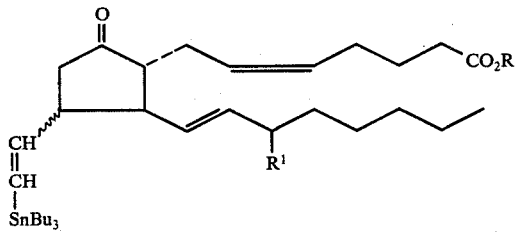

wherein R is hydrogen, alkyl of from 1 to 6 carbon atoms, an alkali metal cation, or a pharmacologically acceptable cation derived from ammonia or a basic amine, and $R^1$ is α-acetoxy or β-acetoxy.

The tangible embodiments of the first composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared and nuclear magnetic resonance spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of being intermediates for the synthesis of the embodiments of the fourth and eighth composition aspects of the invention.

The invention sought to be patented in a second composition aspect residues in the concept of a chemical compound of the structure:

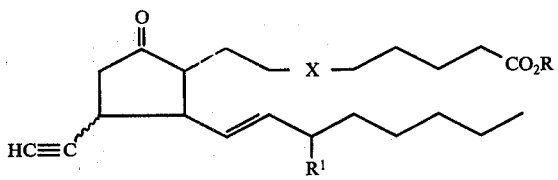

wherein R is hydrogen, alkyl of from 1 to 6 carbon atoms, an alkali metal cation, or a pharmacologically acceptable cation derived from ammonia or a basic amine, $R^1$ is α-hydroxy, β-hydroxy, α-acetoxy or β-acetoxy, and X is a single bond or a cis double bond.

The tangible embodiments of the second composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of snythesis, confirm the structure of the compositions sought to be patented.

The tangible embodiments of the second composition aspect of the invention possess the inherent applied use characteristic of being intermediates for the synthesis of the embodiments of the fourth and eighth composition aspects of the invention. In addition, when X is a cis double bond and $R^1$ is α-hydroxy, the compositions exert hypotensive effects; and when X is a cis double bond and $R^1$ is β-hydroxy and X is a single bond and $R_1$ is α-hydroxy, the compositions exert bronchodilator effects, upon administration to warm-blooded animals. These effects are evidenced by pharmacological evaluation according to standard test procedures.

The invention sought to be patented in a third composition aspect resides in the concept of a chemical compound of the structure:

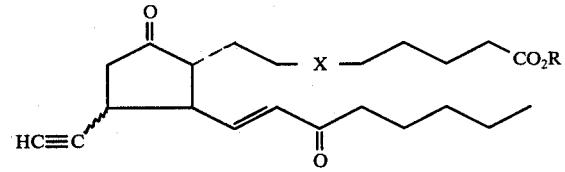

wherein R is hydrogen, alkyl of from 1 to 6 carbon atoms, an alkali metal cation, or a pharmacologically acceptable cation derived from ammonia or a basic amine, and X is a cis double bond, or a single bond.

The tangible embodiments of the third composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention wherein X is a single bond, possess the inherent applied use characteristic of exerting bronchodilator effects, upon administration to warm-blooded animals, as evidenced by pharmacological evaluation according to standard test procedures; and in addition are useful intermediates for the synthesis of the embodiments of the fourth composition aspect of the invention. The tangible embodiments of the third composition aspect of the invention wherein X is a cis double bond possess the inherent applied use characteristic of being intermediates for the synthesis of the embodiments of the eighth composition aspect of the invention.

The invention sought to be patented in a fourth composition aspect resides in the concept of a chemical compound of the structure:

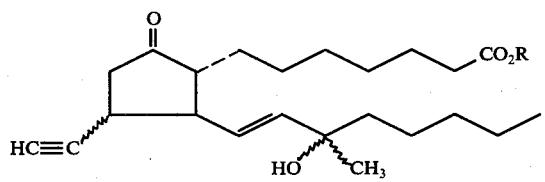

wherein R is hydrogen, alkyl of from 1 to 6 carbon atoms, an alkali metal cation, or a pharmocologically acceptable cation derived from ammonia or a basic amine.

The tangible embodiments of the fourth composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared and nuclear magnetic resonance, spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristics of exerting hypotensive and bronchodilating effects, upon administration to warm-blooded animals. These effects are evidenced by pharmacological evaluation according to standard test procedures.

The invention sought to be patented in a fifth composition aspect resides in the concept of a chemical compound of the structure:

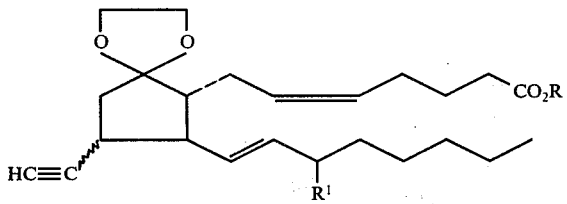

wherein R is hydrogen, alkyl of from 1 to 6 carbon atoms, an alkali metal cation, or a pharmacologically acceptable cation derived from ammonia or a basic amine, and $R^1$ is α-acetoxy, β-acetoxy, α-hydroxy, or β-hydroxy.

The tangible embodiments of the fifth composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical charateristics, taken together with the nature of the starting materials, and the mode of synthesis, confirm the structure of the composition sought to be patented.

The tangible embodiments of the fifth composition aspect of the invention possess the inherent applied use characteristic of being intermediates for the synthesis of the embodiments of the eighth composition aspect of the invention.

The invention sought to be patented in a sixth composition aspect resides in the concept of a chemical compound of the structure:

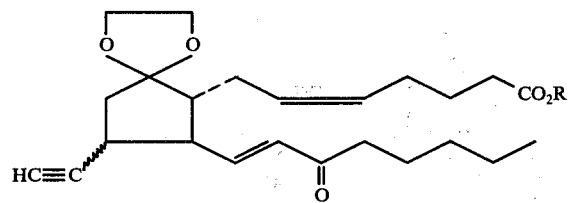

wherein R is hydrogen, alkyl of from 1 to 6 carbon atoms, an alkali metal cation or a pharmacologically acceptable cation derived from ammonia or a basic amine.

The tangible embodiments of the sixth composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the sixth composition aspect of the invention possess the inherent applied use characteristic of being intermediates for the synthesis of the embodiments of the eighth composition aspect of the invention.

The invention sought to be patented in a seventh composition aspect resides in the concept of a chemical compound of the structure:

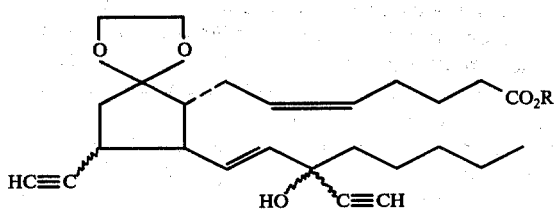

wherein R is hydrogen, alkyl of from 1 to 6 carbon atoms, an alkali metal cation, or a pharmacologically acceptable cation derived from ammonia or a basic amine.

The tangible embodiments of the seventh composition aspect of the invention possess the inherent general physical properties of being clear to yellow oils, and when R is hydrogen or alkyl, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the seventh composition aspect of the invention possess the inherent applied use characteristic of being intermediates for the synthesis of the embodiments of the eighth composition aspect of the invention.

The invention sought to be patented in an eighth composition aspect resides in the concept of a chemical compound of the structure:

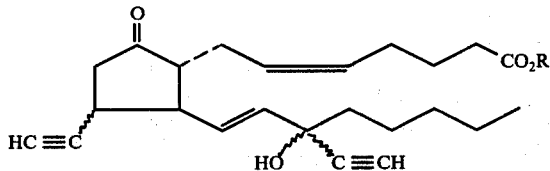

wherein R is hydrogen, alkyl of from 1 to 6 carbon atoms, an alkali metal cation or a pharmacologically acceptable cation derived from ammonia or a basic amine.

The tangible embodiments of the eighth composition aspect of the invention possess the inherent general physical properties of being clear to yellow oils, or crystalline solids and when R is hydrogen or alkyl, are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materaials, and the mode of synthesis, confirm the structure of the compositions sought to be patented.

The tangible embodiments of the eighth composition aspect of the invention possess the inherent applied use characteristics of exerting hypotensive and bronchodilating effects upon administration to warm-blooded animals. These effects are evidenced by pharmacological evaluation according to standard test procedures.

DESCRIPTION OF THE PREFERRED EMBODIMENTS

In describing the synthesis of the compositions of the invention, reference will be made to FIGS. I and II, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of paper, when a dashed line (- - -) is used, the substituent will be understood to be in the α (down) configuration; and when a heavy line (▶) is used, the substituent will be understood to be in the β (up) configuration; and when a wavy line (∿) is used both α and β configurations are contemplated for the substituent. Thus, for example, when a new assymetric center is created by a below-described reaction, for example the addition of a Grignard reagent to a ketone, since both possible configurations for the new substituents will be produced they will be denoted by wavy lines (∿). Both of said isomers, unless otherwise noted, are considered to be full equivalents for the purposes of this invention. The formulae in FIGS. I and II are either free carboxylic acids or esters and it will be obvious to those skilled in the art that the esters may be converted to their respective free acids by, for example, hydrolysis with dilute base and the free acids may readily be esterified as for example, with diazomethane, or with an alkanol and the proper catalyst or the free acids may be converted to an alkali metal or basic amine salt. The esters, salts and free acids are considered to be full equivalents for the purposes of the invention. Finally, the use of specific embodiments of FIGS. I and II to illustrate the invention is merely descriptive and is not intended to delimit the scope of the invention.

Referring now to FIG. I, the starting materials of formula I $PGA_2$, methyl ester, acetate and its 15-epimer are both known compounds. Thus, 15-epi-$PGA_2$-methyl ester, acetate may be isolated from *Plexaura homomalla* as described by Weinheimer and Spraggins, Tet. Letters, 59, 5185 (1969); and $PGA_2$, methyl ester from which $PGA_2$, methyl ester, acetate is readily prepared is described by Bundy et al., Annals of the N.Y. Academy of Sciences, 180, 76 (1971).

Compounds of formula II are prepared by 1,4 conjugate addition of trans-1,2-bis(tri-n-butylstannyl)ethylene to the α, β-unsaturated ketone system of the starting material I. This addition is described in other systems by E. J. Corey and R. H. Wollenberg, J. Am. Chem. Soc., 96, 558 (1974). The compounds of formula II may next be selectively hydrogenated at the C-5,6 double bond by use of tris(triphenylphosphine)rhodium chloride producing the $PGE_1$ series of intermediates or the C-5,6-double bond may be left intact so that the $PGE_2$ intermediates can be prepared. For reasons of convenience the preparation of the $PGE_1$ intermediates and products will be described; however, as evidenced by the working examples, the reactions and reaction conditions are substantially equivalent in the $PGE_2$ series. The compound of formula II, after reduction of the C-5 double bond is treated with lead tetraacetate in, for example, acetonitrile at room temperature producing compound IIIb. Removal of both ester functions of IIIb by reaction with dilute base, for example, dilute methanolic sodium hydroxide solution produces IVb. Oxidation of IVb with the Jones Reagent produces the 15-ketone, Vb which is treated with a methyl metallic reagent, for example, methyl magnesium bromide producing the tertiary alcohol VIb.

As previously stated supra, the 5,6-cis double bond series of compounds (i.e. IIIa through VIa) may be prepared by substantially equivalent reactions and procedures.

Referring now to FIG. II, the 9-ketone function of the starting material IIIa (described in FIG. I) is first protected by, for example, formation of the ethylene ketal by treatment with ethylene glycol producing compound VII. The ester groups of VII are next removed by treatment with dilute base solution, for example, dilute methanolic sodium hydroxide solution and the 15-hydroxyl group is oxidized with, for example, Jones Reagent producing VIII. Alternatively VIII may be prepared by selective ketalization of the 9-ketone function of Va (see FIG. I) with ethylene glycol. The ketone VIII is next treated with an ethynyl metallic reagent, for example, ethynyl magnesium bromide producing the tertiary alcohol IX. The ketal protecting group of IX is next removed by treatment with dilute acid, for example, dilute acetic acid solution producing the ketone X.

In the above-described processes, the configuration of the 15-hydroxy substituent in the starting materials is not critical since this position is oxidized to a ketone and both the α and β hydroxy substituents will be seen to produce the same ketone (see especially the conversions of IV to V and VII to VIII). Thus, PGA$_2$ and 15-epi-PGA$_2$ (and their corresponding esters) are considered substantial equivalent starting materials for the preparation of the instant compounds. The introduction of the C-11 ethynyl group is presumed to be non-stereospecific thus the compounds containing this substituent are presumed to be isomeric mixtures at C-11 and the bond for this substituent is thus represented by a wavy ⁓line.

When used herein and in the appended claims, the term "alkali metal" includes, for example, sodium, potassium, lithium, and the like. A "pharmacologically acceptable cation derived from ammonia or a basic amine" contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

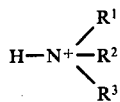

wherein $R^1$, $R^2$, and $R^3$, independently, are hydrogen, alkyl of from 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to 3 carbon atoms, or monocarbocyclicarylhydroxyalkyl of from about 7 to about 15 carbon atoms or, when taken together with the nitrogen atom to which they are attached, any two of $R^1$, $R^2$, and $R^3$ form part of a 5 to 6-membered heterocyclic ring containing carbon, hydrogen, oxygen, nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and tri-methylammonium, mono-, di-, and triethylammonium, mono-, di-, and tripropylammonium (iso and normal), ethyldimethylammonium, benzyldimethylammonium, cyclohexylammonium, benzylammonium, dibenzylamonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris-(hydroxymethyl)methylammonium, phenylmonoethanolammonium, and the like.

The following examples further illustrate the best mode contemplated by the inventor for the practice of the invention.

EXAMPLE 1

7-(2β-[(3R)-3-Hydroxy-Trans-1-Octenyl]-5-Oxo-(3RS)-3-[2-Tri-n-Butyltinethenyl]-1α-Cyclopentyl)-Cis-5-Heptenoic Acid, Methyl Ester, Acetate Cool a solution of 4.67 g. of trans-1,2-bis(tri-n-butylstannyl)ethylene in 25 ml. of tetrahydrofuran under nitrogen to −80° in a dry ice-acetone bath, add 4.8 ml. of 1.6 M n-butyl lithium and stir the mixture for 2 hours. Add a solution of 1.0 g. of pentynyl copper and 2.51 g. of hexamethylphosphorous triamide in 10 ml. of tetrahydrofuran and stir the mixture at −80° for 45 minutes under nitrogen. Add a solution of 3.0 g. of 15-epi-PGA$_2$, methyl ester, acetate in 10 ml. of tetrahydrofuran and stir at −80° for 30 minutes and at −40° for 30 minutes. Dilute the reaction mixture with saturated ammonium sulfate solution and extract with ether. Wash the extract with 100 ml. of ice-cold 2% sulfuric acid, separate and filter the ether solution through Celite. Wash the filtrate with 5% sodium bicarbonate, water, dry over sodium sulfate and evaporate the solvent. Chromatograph the residue on silica with 10% ethyl acetate in hexane to obtain 2.1 g. of 7-(2β-[(3R)-3-hydroxy-trans-1-ocetenyl]-5-oxo(3RS)-3-[2-tri-n-butyltinethenyl]-1α-cyclopentyl)-cis-5-heptenoic acid, methyl ester, acetate as an oil, λmax$^{film}$ 3.45, 5.7, 6.2, 7.2, 8.0, 9.75 μ.

NMR Analysis: δ5.8 (m, 2, CH=CH—Sn), 5.3 (m, 5, C-5,6,13,14,15-H), 3.6 (s, 3, OCH$_3$)$_3$2.0 (s, COCH$_3$) ppm.

EXAMPLE 2

7-(2β-[(3S)-3-Hydroxy-Trans-1-Octenyl]-5-Oxo-(3RS)-3-[2-Tri-n-Butyltinethenyl]-1α-Cyclopentyl)-Cis-5-Heptenoic Acid, Methyl Ester, Acetate Treat 13.3 of PGA$_2$, methyl ester, acetate as in Example 1 to obtain 14.3 g. of 7-(2β-[3S)-3-hydroxy-trans-1-octenyl]-5-oxo(3RS)-3-[2-tri-n-butyltinethenyl]-1α-cyclopentyl)-cis-5-heptenoic acid, methyl ester, acetate as an oil, λmax$^{film}$ 3.5, 5.75, 7.3, 8.05, 9.85 μ.

NMR Analysis: δ5.9 (m, 2, CH=CH—Sn), 5.4 (m, 5, C-5,6,13,14,15-H), 3.6 (s, 3, OCH₃), 2.0 (s, COCH₃) ppm.
Mass Spectral Analysis: M+ —Bu at m/e 650.

EXAMPLE 3

7-([3RS]-3-Ethynyl-2β-[(3R)-3-Hydroxy-Trans-1-Octenyl]-5-Oxo-1α-Cyclopentyl)-Cis-5-Heptenoic Acid, Methyl Ester, Acetate Treat a solution of 5.0 g. of 7-(2β-[(3R)-3-hydroxy-trans-1-octenyl]-5-oxo-(3RS)-3-[2-tri-n-butyltinethenyl]-1α-cyclopentyl)-cis-5-heptenoic acid, methyl ester, acetate in 70 ml. of acetonitrile with 6.3 g. of lead tetraacetate and stir the mixture at 25° for 6 hours. Dilute the reaction mixture with ether, filter and evaporate. Dissolve the residue in 20% ethyl acetate in hexane, filter through 100 g. of alumina (Act. 3, Neutral) and evaporate the solvents. Chromatograph the residue on silica with 10% ethyl acetate in hexane to obtain 2.0 g. of 7-([3RS]-3-ethynyl-2β-[(3R)-3-hydroxytrans-1-octenyl]-5-oxo-1β-cyclopentyl)-cis-5-heptenoic acid, methyl ester, acetate as an oil, $\lambda max^{film}$ 3.0, 3.4, 4.7 (weak), 5.65, 7.15, 7.9, 9.6 μ.

NMR Analysis: β5.6 (m, 2, 13 and 14-H), 5.4 (m, 3, C-5,6,15-H), 3.66 (s, 3, OCH₃), 2.0 (s, COCH₃) ppm.
Mass Spectral Analysis: M+ —HAc at m/e 356, M+ —HAc—OCH₃ at m/e
325.2155 (theory 325.2166).
Analysis for: C, 72.08; H, 8.71.
Found: C, 72.42; H, 8.85.

EXAMPLE 4

7-([3RS]-3-Ethynyl-2β-[(3S)-3-Hydroxy-Trans-1-Ocetenyl]-5-Oxo-1α-Cyclopentyl)-Cis-5-Heptenoic Acid, Methyl Ester, Acetate Treat 4.6 g. of 7-(2β-[(3S)-3-hydroxy-trans-1-octenyl]-5-oxo-(3RS)-3-[2-tri-n-butyltinethenyl]-1α-cyclopentyl)-cis-5-heptenoic acid, methyl ester, acetate according to the procedure of Example 3 to obtain 0.8 g. of 7-([3RS]-3-ethynyl-2β-[(3S)-3-hydroxytrans-1-octenyl]-5-oxo-1α-cyclopentyl)-cis-5-heptenoic acid, methyl ester, acetate as an oil, $\lambda max^{film}$ 3.05, 3.5, 5.75, 7.3, 8.05, 9.8 μ.

NMR Analysis: δ 5.7 (m, 2, 13 and 14-H), 5.4 (m, 3, C-5,6,15-H), 3.0 (s, 3, OCH₃), 2.1 (s, COCH₃) ppm.
Mass Spectral Analysis: M+ —HAc m/e 356.2359 (theory 356.2351).

EXAMPLE 5

(3RS)-3-Ethynyl-2β-[(3R)-3-Hydroxy-Trans-1-Octenyl]-5-Oxo-1α-Cyclopentane Heptanoic Acid, Methyl Ester, Acetate Hydrogenate a solution of 5.3 g. of 7-(2β-[(3R)-3-hydroxy-trans-1-octenyl]-5-oxo-(3RS)-3-[2-tri-n-butyltinethenyl)-1α-cyclopentyl)-cis-5-heptenoic acid, methyl ester, acetate and 2.5 g. of tris (triphenylphosphine) rhodium chloride in 400 ml. of 1:1 benzene:ethanol at 25° and atmospheric pressure until 2 equivalents of hydrogen are absorbed. Evaporate the solvents and chromatograph the residue on silica with 10% ethyl acetate in hexane to obtain 3.3 g. of the crude intermediate. Dissolve the intermediate in 50 ml. of acetonitrile, add 4.03 g. of lead tetra-acetate and stir the mixture at 25° for 6 hours under nitrogen. Dilute the reaction mixture with ether, filter and evaporate the solvents. Dissolve the residue in 20% ethyl acetate in hexane, filter through 100 g. of alumina (Neutral, Act. 3) and evaporate the solvents. Chromatograph the residue on silica with 10% ethyl acetate in hexane to obtain (3RS)-3-ethynyl-2β-[(3R)-3-hydroxy-trans-1-octenyl]-5-oxo-1α-cyclopentane heptenoic acid, methyl ester, acetate as an oil, $\lambda max^{film}$ 3.1, 3.5, 4.75 (weak), 5.75, 7.3, 8.1, 9.8 μ.

NMR Analysis: δ5.6 (m, 2, 13 and 14-H), 5.3 (m, 1, 15-H), 3.7 (s, 3, OCH₃), 2.0 (s, COCH₃) ppm.
Mass Spectral Analysis: M+ —HAc—OCH₃ at m/e 327.2312 (theory 327.2323).

EXAMPLE 6

(3RS)-3-Ethynyl-2β-[(3S)-3-Hydroxy-Trans-1-Octenyl]-5-Oxo-1α-Cyclopentane Heptanoic Acid, Methyl Ester, Acetate Treat 5.0 g. of 7-(2β-[3S]-3-hydroxy-trans-1-octenyl]-5-oxo-(3RS)-3-(2-tri-n-butyltinethenyl)-1α-cyclopentyl)-cis-5-heptenoic acid, methyl ester, acetate according to the procedure of Example 5, to obtain 0.83 g. of (3RS)-3-ethynyl-2β-[(3S)-3-hydroxytrans-1-octenyl]-5-oxo-1α-cyclopentane heptanoic acid, methyl ester, acetate as an oil, $\lambda max^{film}$ 3.1, 3.5, 4.7 (weak), 5.8, 7.4, 8.2, 9.9 μ.

NMR Analysis: δ5.6 (m, 2, 13 and 14-H), 5.2 (m, 1, 15-H), 3.6 (s,

3, OCH₃), 2.0 (s, COCH₃) ppm.
Mass Spectral Analysis: M+ at m/e 418, M+ —HAc at m/e 358.2502 (theory 358.2507).

EXAMPLE 7

7-([3RS]-3-Ethynyl-2β-[(3S)-3-Hydroxy-Trans-1-Octenyl]-5-Oxo-1α-Cyclopentyl)-Cis-5-Heptenoic Acid Stir a solution of 0.7 g. of 7-([3RS]-3-ethynyl-2β-[(3S)-3-hydroxy-trans-1-octenyl]-5-oxo-1α-cyclopentyl)-cis-5-heptenoic acid, methyl ester, acetate in 25 ml. of methanol and 25 ml. of 1N sodium hydroxide for 1.5 hours at 25° under nitrogen. Dilute the mixture with water, acidify with hydrochloric acid and extract with ether. Wash and dry the extract, evaporate the solvent and chromatograph the residue on silica with 30% ethyl acetate in hexane to obtain 0.54 g. of 7-([3RS]-3-ethynyl-2β-[(3S)-3-hydroxy-trans-1-octenyl]-5-oxo-1β-cyclopentyl)-cis-5-heptenoic acid as an oil, $\lambda max^{film}$ 3.5, 4.75, 5.8, 7.1, 8.1, 8.7, 10.3 μ.

NMR Analysis: δ5.7 (m, 2, 13 and 14-H), 5.4 (m, 2, 5 and 6-H), 4.2 (m, 1, 15-H)ppm.
Mass Spectral Analysis: M+ —H₂O at m/e 342.2192 (theory 342.2194).

EXAMPLE 8

7-([3RS]-3-Ethynyl-2β-[(3R)-3-Hydroxy-Trans-1-Octenyl]-5-Oxo-1β-Cyclopentyl)-Cis-5-Heptenoic Acid Treat 0.42 g. of 7-([3RS]-3-ethynyl-2β-[(3R)-3-hydroxytrans-1-octenyl]-5-oxo-1α-cyclopentyl)-cis-5-heptenoic acid, methyl ester, acetate according to the procedure of Example 7 to obtain 0.18 g. of 7-([3RS]-3-ethynyl-2β-[(3R)-3-hydroxy-trans-1-octenyl]-5-oxo-1β-cyclopentyl)-cis-5-heptenoic acid as an oil, $\lambda max^{film}$ 3.5, 4.7, 5.7, 7.0, 8.0, 8.6, 10.3 μ.

NMR Analysis: δ5.2–5.8 (m, 4, olefinic-H), 4.2 (m, 1, 15-H) ppm.

Mass Spectral Analysis: M+ —C₅H₁₁ at m/e 289.1584 (theory 289.1591).

EXAMPLE 9

3α-Ethynyl-2β-[(3S)-3-Hydroxy-Trans-1-Octenyl]-5-Oxo-1α-Cyclopentaneheptanoic Acid Treat 0.65 g. of (3RS)-3-ethynyl-2β-[(3S)-3-hydroxy-trans-1-octenyl]-5-oxo-1α-cyclopentane-heptanoic acid, methyl ester, acetate according to the procedure of Example 7 to obtain 0.35 g. of 3α-ethynyl-2β-[(3S)-3-hydroxy-trans-1-octenyl]-5-oxo-1α-cyclopentaneheptanoic acid, m.p. 82°–84°, $\lambda max^{KBr}$ 2.9, 3.4, 5.7, 7.1, 8.5, 10.3 μ.

NMR Analysis: δ6.9 (s, 2, OH), 5.7 (m, 2, 13 and 14-H), 4.2 (m, 1, 15-H) ppm.

Mass Spectral Analysis: M+ –$C_5H_{11}$ at m/e 291.1604 (theory 291.1595).

Analysis for: C, 72.89; H, 9.45.
Found: C, 72.58; H, 9.61.

EXAMPLE 10

7-([3RS]-3-Ethynyl-5-Oxo-2β-[3-Oxo-Trans-1-Ocetnyl]-1α-Cyclopentyl)-Cis-5-Heptenoic Acid Treat a solution of 1.5 g. of 7-([3RS]-3-ethynyl-2β-[(3R)-3-hydroxy-trans-1-octenyl]-5-oxo-1α-cyclopentyl)-cis-5-heptenoic acid in 50 ml. of acetone at 0° under nitrogen with 2.5 ml. of Jones Reagent and stir the mixture at 25° under nitrogen for 0.5 hours. Aff. 10 ml. of methanol, dilute the mixture with water and extract with ether. After washing and drying, evaporate the extract and chromatograph the residue on silica with 20% ethyl acetate in hexane to obtain 1.24 g. of 7-([3RS]-3-ethynyl-5-oxo-2β-[3-oxo-trans-1-octenyl]-1α-cyclopentyl)-cis-5-heptenoic acid as an oil, $\lambda max^{film}$ 3.5, 5.7, 5.8, 6.1, 7.0, 8.6, 10.2 μ. UV: $\lambda_{max}$ 227 mμ(ϵ 12,100). NMR Analysis:δ6.7 (q, J=4.5, 12, 13-H), 6.2 (d, J=12, 14-H), 5.3 (m, 2, 5 and 6-H) ppm.

Mass Spectral Analysis: M+ at m/e 358, M+ —$H_2O$ at m/e 340.2014 (theory 340.2038).

EXAMPLE 11

(3RS)-3-Ethynyl-5-Oxo-2β-(3-Oxo-Trans-1-Octenyl)-1α-Cyclopentaneheptanoic Acid

Treat a solution of 0.80 g. of (3RS)-3-ethynyl-2β-[(3R)-3-hydroxy-trans-1-octenyl]-5-oxo-1β-cyclopentane-heptanoic acid, methyl ester, acetate in 20 ml. of methanol with 20 ml. of 1N sodium and stir for 1.5 hours at 25° under nitrogen. Dilute with water, acidify with hydrochloric acid and extract with ether. After washing and drying, evaporate the extract, dissolve the residue in 20 ml. of acetone, and 1.0 ml. of Jones Reagent and stir at 0° for 0.5 hours under nitrogen. Add 5 ml. of methanol, dilute with water and extract with ether. After washing and drying, evaporate the extract and chromatograph the residue on silica with 20% ethyl acetate in hexane to obtain (3RS)-3-ethynyl-5-oxo-2β-(3-oxo-trans-1-octenyl)-1α-cyclopentaneheptanoic acid as an oil, $\lambda max^{film}$ 3.5, 5.8, 6.1, 7.1, 10.2 μ.

NMR Analysis: δ6.8 (2, J=6, 16, 13-H), 6.3 (d, J=16, 14-H) ppm.

Mass Spectral Analysis: M+ —$H_2O$—$C_5H_{11}$ at m/e 271.1300 (theory 271.1333).

EXAMPLE 12

7-([3RS]-3-Ethynyl-2β-[(3RS)-3-Hydroxy-3-Methyl-Trans-1-Octenyl]-5-Oxo-1α-Cyclopentyl)-Cis-5-Heptenoic Acid Treat a solution of 1.1 g. of 7-([3RS]-3-ethynyl-5-oxo-2β-[3-oxo-trans-1-octenyl]-1α-cyclopentyl)-cis-5-heptenoic acid in 50 ml. of tetrahydrofuran at 0° with 5.4 ml. of 2.6 M methyl magnesium bromide in ether with stirring at 0° under nitrogen over 1.75 hr. Dilute with water, acidify with acetic acid and extract with ether. After washing and drying, evaporate the extract and chromatograph the residue on silica with 30% ethyl acetate in hexane to obtain 0.38 g. of 7-([3RS]-3-ethynyl-2β-[3RS)-3-hydroxy-3-methyl-trans-1-octenyl]-5-oxo-1α-cyclopentyl)-cis-5-heptenoic acid as an oil, $\lambda max^{film}$ 3.5, 4.8, 5.8, 8.1, 8.7, 10.3 μ.

NMR Analysis: δ 5.3–5.8 (m, 4, olefinic-H), 1.3 (s, 15-$CH_3$) ppm.

Mass Spectral Analysis: M+ —$H_2O$—$C_5H_{11}$ at m/e 285.1499 (theory 285.1490).

EXAMPLE 13

(3RS)-3-Ethynyl-2β[(3RS)-3-Hydroxy-3-Methyl-Trans-1-Octenyl]-5-Oxo-1α-cyclopentane-Heptanoic Acid Treat 0.51 g. of (3RS)-3-ethynyl-5-oxo-2β-(3-oxo-trans-1-octenyl)-1α-cyclopentane-heptanoic acid according to the procedure of Example 12 to obtain 0.12 g. of (3RS)-3-ethynyl-2β-[(3RS)-3-hydroxy-3-methyl-trans-1-octenyl]-5-oxo-1α-cyclopentane-heptanoic acid as an oil, $\lambda max^{film}$ 3.4, 4.7, 5.8, 6.8, 8.1, 10.3 μ.

NMR Analysis: δ6.4 (s, 2, OH), 5.8 (m, 2, 13 and 14-H), 1.4 (s, 15-$CH_3$) ppm.

EXAMPLE 14

7-([8RS]-8-Ethynyl-7-[(3R)-3-Hydroxy-Trans-1-Octenyl]-1,4-Dioxaspiro-[4.4]Non-6α-yl)-Cis-5-Heptenoic Acid, Methyl Ester, Acetate Reflux a solution of 1.4 g. of 7-([3RS]-3-ethynyl-2β-[(3R)-3-hydroxy-trans-1-octenyl]-5-oxo-1α-cyclopentyl)-cis-5-heptenoic acid, methyl ester, acetate and 0.15 g. of p-toluenesulfonic acid in 150 ml. of benzene and 15 ml. ethylene glycol with a Dean-Stark water separator for 21 hours under nitrogen. Cool and dilute the mixture with ether. After washing and drying, evaporate the solvents and chromatograph the residue on silica to obtain 1.06 g. of 7-([8RS]-3-ethynyl-7-[(3R)-3-hydroxy-trans-1-octenyl]-1,4-dioxaspiro[4.4]non-6α-yl)-cis-5-heptenoic acid, methyl ester, acetate as an oil, $\lambda max^{film}$ 3.5, 5.75, 7.3, 8.0, 9.8 μ.

NMR Analysis: δ5.1–5.7 (m, 5, C-5, 6, 13, 14, 15-H), 3.9 (s, 4, ketal), 3.7 (s, 3, $OCH_3$), 2.1 (s, $COCH_3$) ppm.

Mass Spectral Analysis: M+ —HAc at m/e 400.2599 (theory 400.2613).

EXAMPLE 15

7-([3RS]-8-Ethynyl-7-[3-Oxo-Trans-1-Octenyl]-1,4-Dioxaspiro[4.4]Non-6α-yl)-Cis-5-Heptenoic Acid Stir a solution of 1.0 g. of 7-([3RS]-8-ethynyl-7-[(3R)-3-hydroxy-trans-1-octenyl]-1,4-dioxaspiro[4.4]non-6α-yl)-cis-5-heptenoic acid, methyl ester, acetate in 25 ml. of methanol and 25 ml. of 1N-sodium hydroxide at 25° for 3 hours under nitrogen. Dilute the mixture with water, acidify with acetic acid and extract with ether. After washing and drying, evaporate the extract and dissolve the residue in 50 ml. of acetate at −20° under nitrogen. Add 0.85 ml. of Jones Reagent and stir and mixture for 10 minutes at −20° under nitrogen. Add 10 ml. of methanol, 15 ml. of dilute sodium carbonate, dilute with water, acidify with acetic acid and extract with ether. After washing and drying, evaporate the extract and chromatograph the residue on silica with 20% ethyl acetate in hexane to obtain 0.6 g. of 7-([8RS]-8-ethynyl-7-[3-oxo-trans-1-octenyl]-1,4-dioxaspiro[4.4]-non-6α-yl)-cis-5-heptenoic acid as an oil, λmax$^{film}$ 3.4, 5.8, 5.9, 6.1, 8.6, 9.6, 10.1, 10.5 μ.

NMR Analysis: δ6.7 (q, J=7, 16 cps, 13-H), 6.2 (d, J=16, 14-H), 5.3 (m, 2, 5 and 6-H), 3.9 (s, 4, ketal) ppm.

Mass Spectral Analysis: M+ at m/e 402.2416 (theory 402.2404).

EXAMPLE 16

7-(8RS]-8-Ethynyl-7β-[(3RS)-3-Ethynyl-3-Hydroxy-Trans-1-Octenyl]-1,4-Dioxaspiro[4.4]Non-6α-yl)-Cis-5-Heptenoic Acid Add a solution of 0.6 g. of 7-([3RS]-8-ethynyl-7-[3-oxo-trans-1-octenyl]-1,4-dioxaspiro[4.4]non-6α-yl)-cis-5-heptenoic acid in 15 ml. of tetrahydrofuran to a solution of ethynyl magnesium bromide (prepared from 5.35 ml. of 2.8 M methyl magnesium bromide and excess acetylene) in 65 ml. of tetrahydrofuran and stir at 25° for 15 minutes. Dilute the reaction mixture with water, acidify with acetic acid and extract with ether. After washing and drying, evaporate the extract and chromatography the residue on silica with 20% ethyl acetate in hexane to obtain 0.32 g. of 7-([8RS]-8-ethynyl-7β-[(3RS)-3-ethynyl-3-hydroxy-trans-1-octenyl]-1,4-dioxaspiro[4.4]-non-6α-yl)-cis-5-heptenoic acid as an oil, λmax$^{film}$ 3.5, 4.7, 5.9, 8.7, 9.6, 10.3 μ.

NMR Analysis: δ5.8 (m, 2, 13 and 14-H), 5.4 (m, 2, 5 and 6-H), 3.9 (s, 4, ketal) ppm.

Mass Spectral Analysis: M+ at m/e 428, M+ —C$_5$H$_{11}$ at m/e 357.1700 (theory 357.1702).

EXAMPLE 17

7-[(3RS)-3-Ethynyl-2β-[(3RS)-3-Ethynyl-3-Hydroxy-Trans-1-Octenyl]-5-Oxo-1α-Cyclopentyl]-Cis-5-Heptenoic Acid Keep a solution of 0.385 g. of 7-([3RS]-8-ethynyl-7-[(3RS)-3-ethynyl-3-hydroxy-trans-1-octenyl]-1,4-dioxaspiro[4.4]non-6α-yl)-cis-5-heptenoic acid in 20 ml. of acetic acid and 10 ml. of water at 25° for 6 hours under nitrogen. Dilute the mixture with water and extract with ether. After washing and drying, evaporate the extract and chromatograph the residue on silica with 20% ethyl acetate in hexane to obtain 0.162 g. of 7-[(3RS)-3-ethynyl-2β-[(3RS)-3-ethynyl-3-hydroxy-trans-1-octenyl]-5-oxo-1α-cyclopentyl]-cis-5-heptenoic acid as an oil, λmax$^{film}$ 3.5, 4.8, 5.8, 7.1, 8.7, 10.3 μ.

NMR Analysis: δ5.8 (m, 2, 13 and 14-H), 5.4 (m, 2, 5 and 6-H) ppm.

Mass Spectral Analysis: M+ at m/e 384, M+—C$_5$H$_{11}$ at m/e 313.1408 (theory 313.1439).

EXAMPLE 18

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 25 micrograms, and preferably from about 0.15 to about 15 micrograms. The bronchodilation produced upon aerosol inhalation can be observed by the method of Rosenthale et al., J. Pharmacol. Exp. Ther., 178, 541 (1971). Using this procedure the following results were obtained:

| Compound | Dose (μg) | Percent Inhibition of the bronchoconstricting effects of a standard dose* of acetylcholine |
|---|---|---|
| 7-[(3RS)-3-ethynyl-2β-([3R]-3-hydroxy-trans-1-octenyl)-5-oxo-1α-cyclopentyl]-cis-5-heptenoic acid | 1.50<br>15 | 43<br>68 |
| (3RS)-3-ethynyl-5-oxo-2β-(3-oxo-trans-1-octenyl)-1α-cyclopentaneheptanoic acid | 1.50<br>15 | 36<br>75 |
| (3RS)-3-ethynyl-2β-[(BRS)-3-hydroxy-3-methyl-trans-1-octenyl]-5-oxo-1β-cyclopentane heptanoic acid | 0.15<br>1.50<br>15 | 54<br>56<br>37 |
| 7-[(3RS)-3-ethynyl-2β-([3RS]-3-ethynyl-3-hydroxy-trans-1-octenyl)-5-oxo-1β-cyclopentyl]-cis-5-heptenoic acid | .015<br>.15<br>1.50 | 42<br>56<br>86 |
| 3α-ethynyl-2β-[(3S)-3-hydroxy-trans-1-octenyl]-5-oxo-1α-cyclopentaneheptanoic acid | .015<br>.15<br>1.50<br>15.0 | 28<br>52<br>58<br>76 |

*The dose (i.v.) of acetylcholine which produces a ca. 30% bronchoconstriction.

EXAMPLE 19

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 μg/kg. to about 200 μg/kg. and preferably from about 10 μg/kg. to about 100 μg/kg. Using this procedure the following results were obtained.

| Compound | Dose (μg/kg.) | Δ B.P. (mm. mg) |
|---|---|---|
| 7-[(3RS)-3-ethynyl-2β-([3S]-3-hydroxy-trans-1-octenyl)-5-oxo-1α-cyclopentyl]-cis-5- | 100 | −31 |

| Compound | Dose (μg/kg.) | Δ B.P. (mm. mg) |
|---|---|---|
| heptenoic acid (3RS)-3-ethynyl-2β-[(3RS)-3-hydroxy-3-methyl-trans-1-octenyl]-5-oxo-1α-cyclopentane-heptanoic acid | 100 | −16 |
| 7-[(3RS)-3-ethynyl-2β-([3RS]-3-ethynyl-3-hydroxy-trans-1-octenyl)-5-oxo-1α-cyclopentyl]-cis-5-heptenoic acid | 100 | −41 |

*Average of two animals.

The subject matter which the Applicant regards as his invention is particularly pointed out and distinctly claimed as follows:

1. A chemical compound of the structure:

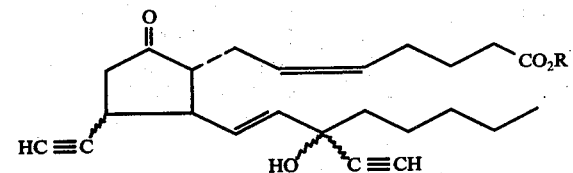

wherein R is hydrogen, alkyl of from 1 to 6 carbon atoms, an alkali metal cation or a pharmacologically acceptable cation derived from ammonia or a basic amine.

2. The chemical compound of claim 1 wherein R is hydrogen.

* * * * *